United States Patent [19]

Witzel

[11] Patent Number: 4,619,659
[45] Date of Patent: Oct. 28, 1986

[54] HIP ENDOPROSTHESIS

[76] Inventor: Ulrich Witzel, Wittener Str. 73d, D-5600 Wuppertal, Fed. Rep. of Germany

[21] Appl. No.: 653,519

[22] Filed: Sep. 21, 1984

[30] Foreign Application Priority Data

Sep. 21, 1983 [DE] Fed. Rep. of Germany ....... 3334058

[51] Int. Cl.$^4$ .............................................. A61F 2/32
[52] U.S. Cl. ...................................................... 623/23
[58] Field of Search ....................... 3/1.9, 1.91, 1.911, 3/1.912, 1.913; 128/92 C, 92 CA

[56] References Cited

U.S. PATENT DOCUMENTS

| 4,280,233 | 7/1981 | Raab ..................................... | 3/1.913 |
| 4,283,799 | 8/1981 | Pratt, Jr. et al. ..................... | 3/1.913 |
| 4,352,212 | 10/1982 | Greene et al. ......................... | 3/1.91 |
| 4,454,612 | 6/1984 | McDaniels et al. .................. | 3/1.913 |

FOREIGN PATENT DOCUMENTS

| 2247721 | 4/1974 | Fed. Rep. of Germany ....... | 3/1.912 |
| 2734249 | 2/1979 | Fed. Rep. of Germany ....... | 623/22 |
| 2933237 | 3/1981 | Fed. Rep. of Germany ....... | 3/1.91 |

*Primary Examiner*—Richard J. Apley
*Assistant Examiner*—David J. Isabella
*Attorney, Agent, or Firm*—Karl F. Ross; Herbert Dubno

[57] ABSTRACT

A hip endoprosthesis for mounting in a distally tapering recess that opens at the proximal end of a femur has a nonmetallic sheath imbedded in the recess so as to be generally integral with the femur and having an inner surface with a distally tapering proximal portion and a uniform-section distal portion. A ball shaped to fit into an acetabulum is carried on a neck in turn formed unitarily of metal with the ball with a stem engaged in the sheath and having an outer surface with a proximal portion complementary to and tightly fitted in the proximal surface portion of the sheath surface and a distal portion slidable in the distal surface portion of the sheath surface. Thus relative motion of the proximal surface portions is impossible but relative sliding motion of the distal surface portions is possible. The main load is transmitted directly to the head of the femur, where it is normally applied, and the transverse load is transmitted through the sliding joint to a more distal portion of the femur, where this type of load is also normally received.

12 Claims, 16 Drawing Figures

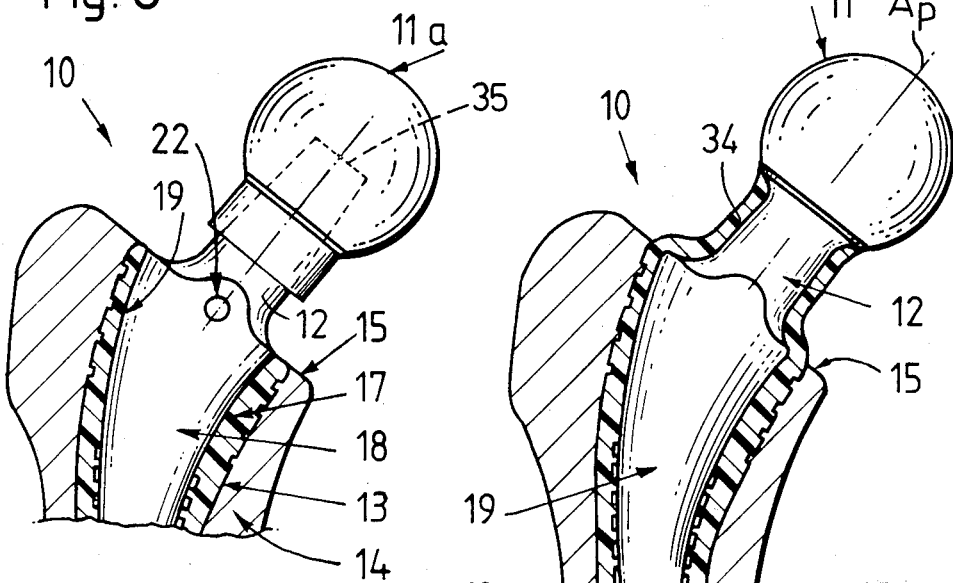
Fig. 6
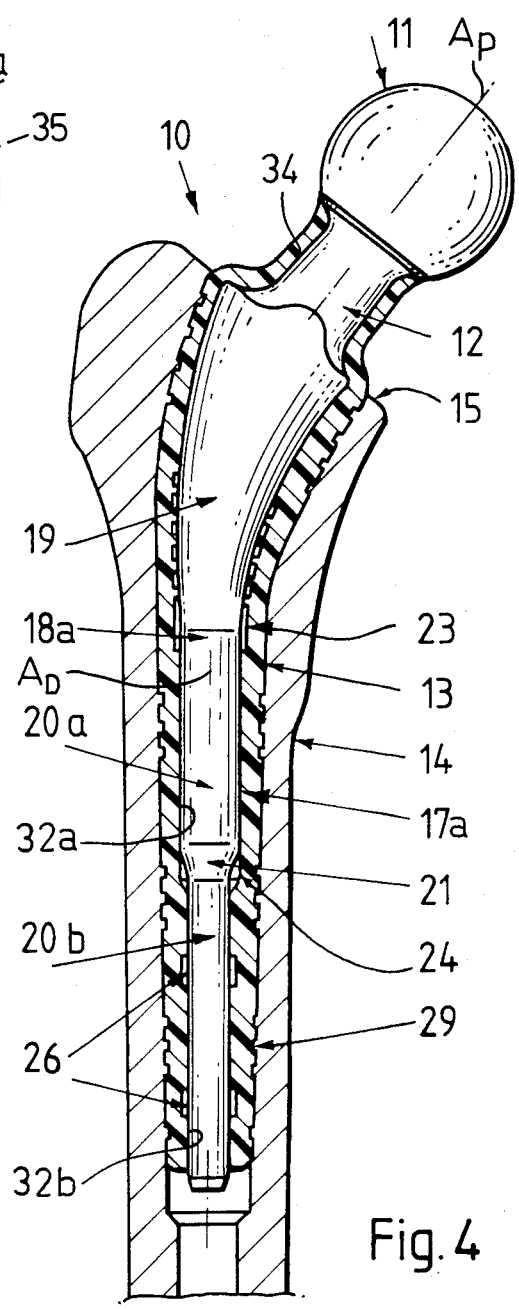
Fig. 5
Fig. 4

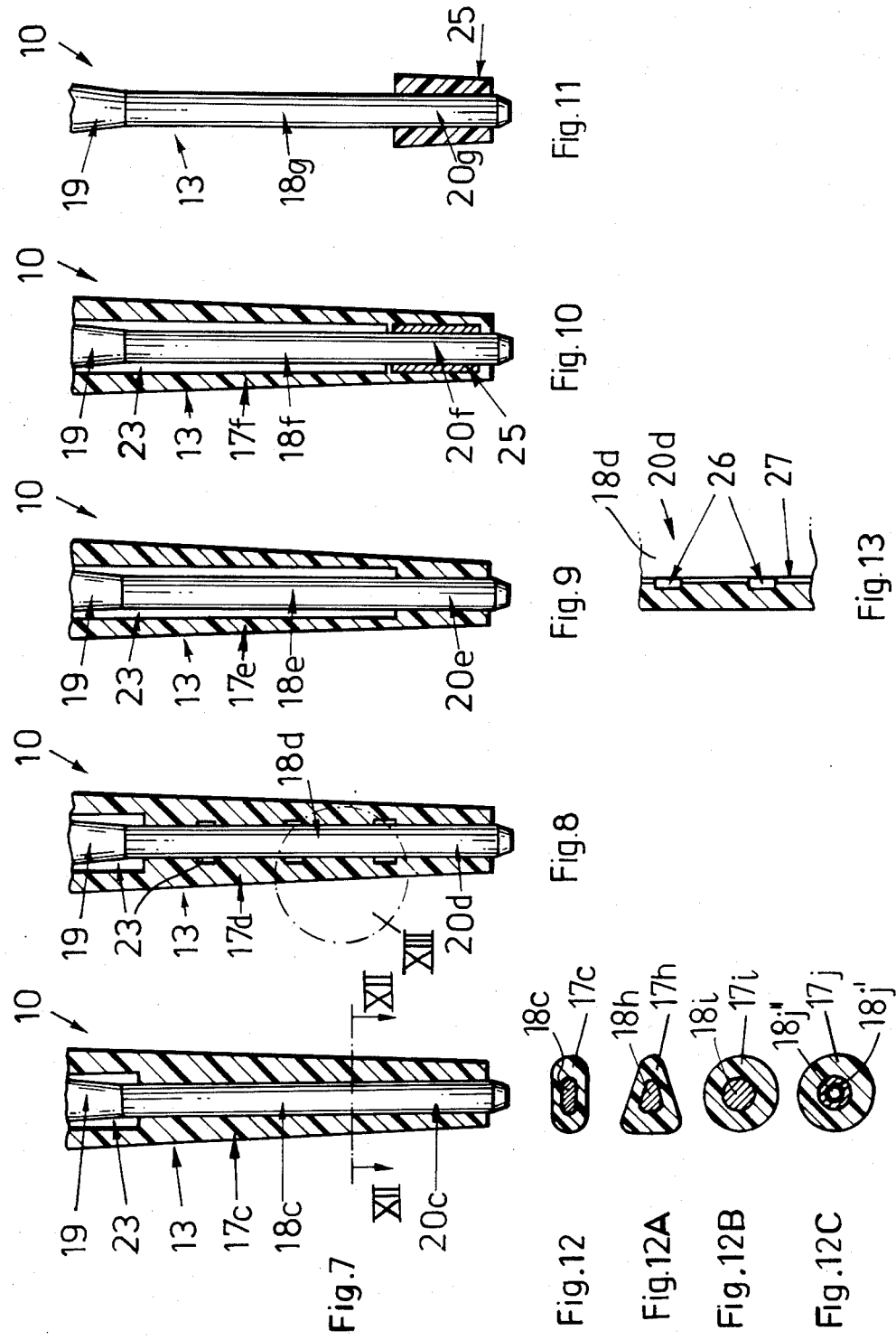

HIP ENDOPROSTHESIS

FIELD OF THE INVENTION

The present invention relates to a prosthetic hip joint. More particularly this invention concerns the hip-joint endoprosthesis, the inner ball part that is carried on the upper end of the femur.

BACKGROUND OF THE INVENTION

An endoprosthesis for a hip joint normally comprises a ball shaped to fit into a natural or prosthetic acetabulum, a neck extending down and out from this ball, and a stem fitting down into the femur, all made unitarily of a high-strength metallic alloy. The stem tapers downward away from the ball and is received in a normally synthetic-resin sheath whose entire outside surface is solidly cemented into the femur along the full length of the stem. The stem is fixed at least partially to the inside surface of the sheath and may in fact be imbedded in the sheath like the sheath is in the femur.

The sheath serves to compensate for the differences in modulus of elasticity of the metal stem, neck, and ball on the one hand and that of the corticalis and spongiosa of the bone on the other. If the metal part were implanted directly in the bone it would be likely to work relative to the bone and come loose. In addition the major forces the joint would be subjected to would be transmitted by the normally lower distal end of the stem to a distal portion of the femur, something that happens whether or not the neck has a collar sitting on the proximal end of the femur.

In order to obtain a homogenous force transfer between the metal part and the sheath, the section of the metal part if made of steel should be reduced relative to that of the synthetic-resin sheath to about 1/67. Such a reduction is practically impossible due to the likelihood of breakage from insufficient dynamic resistance to bending. In order to avoid such a chance of breakage, a substantially thicker stem is employed.

Another problem with the prior-art arrangements in which the main load is transferred by the endoprosthesis to a nonproximal portion of the femur is that the lack of active stimulation of the hard upper end of the femur causes it to atrophy. This atrophy in turn leads to loosening of the proximal end of the endoprosthesis, greatly shortening the service life of the unit and in fact making its replacement quite complex.

OBJECTS OF THE INVENTION

It is therefore an object of the present invention to provide an improved hip endoprosthesis.

Another object is the provision of such a hip endoprosthesis which overcomes the above-given disadvantages, that is which adequately transmits the axial forces and bending moments between the ball and the femur.

A further object is to provide such a prosthesis which emulates human physiology in that the normally vertical axially directed loading of the hip joint is transmitted to the normally upper proximal part of the femur while the normally horizontal bending moment is transmitted to a more distal region that is normally lower, thereby reducing the possibility of bone atrophy.

Yet another object is to provide such a prosthesis that is secured so that its loosening is virtually impossible.

Summary of the Invention

A hip endoprosthesis for mounting in a distally tapering recess that opens at the proximal end of a femur according to the invention has a nonmetallic sheath imbedded in the recess so as to be generally integral with the femur and having an inner surface with a distally tapering proximal portion and a uniform-section distal portion. A ball shaped to fit into an acetabulum is carried on a neck in turn formed unitarily of metal with the ball with a stem engaged in the sheath and having an outer surface with a proximal portion complementary to and tightly fitted in the proximal surface portion of the sheath surface and a distal portion slidable in the distal surface portion of the sheath surface. Thus relative motion of the proximal surface portions is impossible but relative sliding motion of the distal surface portions is possible.

The endoprosthesis of this invention can be considered a permanent implant due to its extremely long service life. The main load is transmitted directly to the head of the femur, where it is normally applied, and the transverse load is transmitted through the sliding joint to a more distal portion of the femur, where this type of load is also normally received. As a result loosening of the distal part of the stem is impossible. In addition since the head of the femur is being actively stimulated, it will not atrophy.

The stem according to this invention can have a pair of relatively telescoping parts. The proximal surface portions are generally frustoconical and the distal surface portions are in the simplest embodiment substantially cylindrical, although other sections are possible.

The inner surface of the sheath of this invention forms an annular compartment between the respective distal and proximal portions, and this compartment can be longer than the distal surface portion of the sheath. An inwardly open groove can form the compartment.

The sheath of this invention can have a lining sleeve forming the distal sheath surface portion and the distal sheath surface portion can be formed with radially inwardly opening grooves containing a lubricant. Similarly at least one of the distal surface portions has a surface coating with a very low coefficient of friction.

The stem distal surface portion can be generally cylindrical and stepped, having an inner large-diameter region and an outer smaller-diameter region. This structure allows the stem to have a bending modulus that closely matches that of the femur.

The stem of this invention is releasably snap-fitted into the sheath so that it can be installed and removed easily, leaving this sheath in as a permanent implant. Such snap fitting can be as simple as tabs formed on the sheath that are engaged into or between radially extending formations on the ball neck or the outer end of the stem.

DESCRIPTION OF THE DRAWINGS

The above and other features and advantages will become more readily apparent from the following, it being understood that any feature described with reference to only one embodiment of the invention can be used where possible with any other embodiment. In the accompanying drawing:

FIG. 4 is a view like FIG. 1 of another embodiment of this invention;

FIG. 5 is a large-scale view of a detail of FIG. 4;

FIG. 6 is a detail view illustrating a variation on the proximal end of the embodiment of FIGS. 4 and 5;

FIGS. 7, 8, 9, 10, and 11 are detail views showing further variations of the distal end of the prosthesis of this invention;

FIG. 12 is a section taken along line XII—XII of FIG. 7;

FIGS. 12A, 12B, and 12C are views like FIG. 12 but showing other stem sections; and FIG. 13 is a view of the detail indicated at XIII in FIG. 8.

SPECIFIC DESCRIPTION

Figure 2:
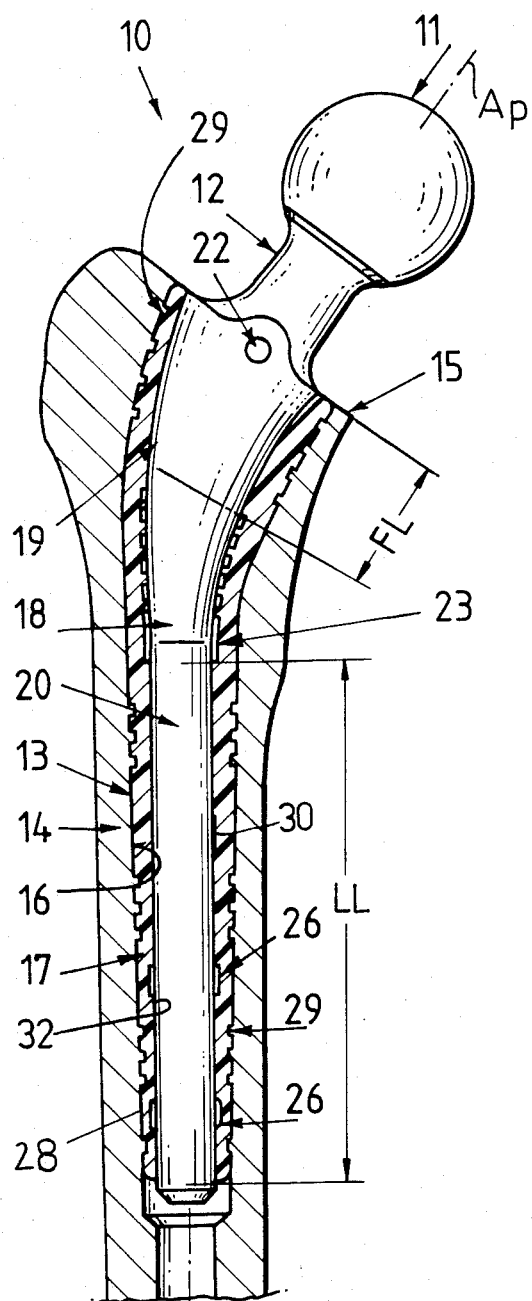
FIG. 2 is an axial section through a first embodiment of the prosthesis of this invention.
Figure 1:
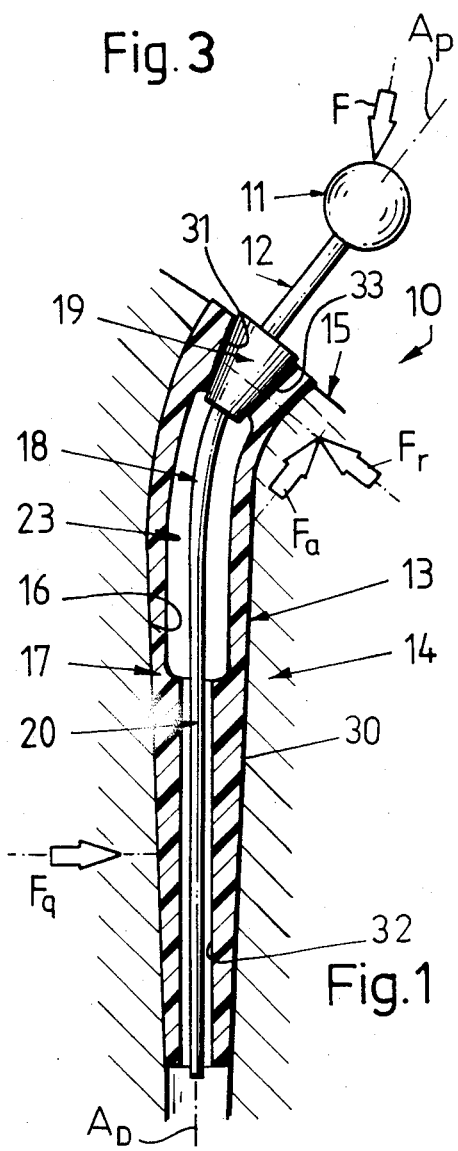
FIG. 1 is mainly diagrammatic axial section through the endoprosthesis according to this invention.

As seen in FIGS. 1 and 2 the endoprosthesis 10 according to this invention basically comprises a spherical ball 11 adapted to fit into the patient's acetabulum, a neck 12 extending radially from the ball 11, and an imbedded part 13 that is seated in a recess 16 formed in the upper end of a femur 14. The neck 12 and ball 11 are centered on a proximal axis $A_P$ which is normally inclined to the horizontal and that projects up through the patient's acetabulum, and the stem 13 is centered on a distal axis $A_D$ which is normally vertical and that extends at an obtuse angle of about 145° to the axis $A_P$. The natural neck and ball are sawed off the femur 14 so that the recess 16 opens proximally at an upper surface 15.

The imbedded part 13 is formed by a central distally tapering stem 18 that is formed unitarily of metal with the neck 12 and ball 11, and a synthetic-resin sheath 17 surrounding the stem 18. This sheath 17 has an outer surface in continuous surface-to-surface contact with the inner surface of the recess 16, and in fact is held therein by a layer 30 of cement that joins the nonrigid sheath 17 integrally to the bone 14.

As shown mainly diagrammatically in FIG. 1 and in more structural detail in FIG. 2, the stem 18 has a generally frustoconical proximally flaring upper surface portion 19 and a cylindrical or uniform-section lower surface portion 20. The proximal surface portion 19 is secured in a complementarily shaped surface portion 31 at the upper end of the interior of the sheath 17 at an interface 33 at which there is annular all-around contact between the surface portions 31 and 19 so that they cannot move relative to each other. The distal end 20 of the stem 18 is, on the other hand, received with slight play so it can slide along a main axis A of the surface portion 20 in a cylindrical inner distal surface portion 32 of the sheath 17 of shape complementary to the uniform-section end surface portion 20. This therefore forms a proximal nonmoving joint FL and a distal sliding joint LL.

Figure 3:
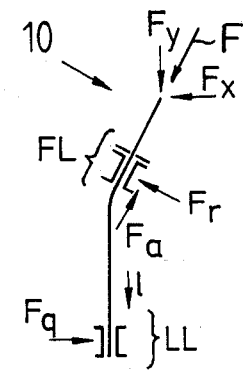
FIG. 3 is a diagram illustrating the instant invention.

Thus, as diagrammed in FIG. 3, the forces F that must be transmitted through the hip-joint prosthesis 10 can be resolved into a downward force $F_y$ and a horizontally outward force $F_x$, both applied to the ball 11. The downward and horizontal forces $F_y$ and $F_x$ are absorbed wholly by the upper end of the calcar femorale, that is the upper end of the femur 14, in the joint FL, countered by radial forces $F_r$ and axial forces $F_a$. As a result this upper end of the femur 14 remains stimulated and will not atrophy.

The horizontal bending moment produced in the joint 10 will be countered by a transverse force $F_q$ in the sliding joint LL, where such a force normally is applied in a leg. Thus the problem with the prior-art joints, that of the stem transmitting axial force to the nonproximal part of the femur at the distal end of the endoprosthesis, is completely eliminated. Such motion, which is the result of the different bending characteristics of the sheath 17 and stem 18, is simply permitted in this region.

Between the surface portions 31 and 32 the inner surface of the sheath 17 is formed with a radially inwardly open groove 23 that clearly delimits the nonmoving joint FL from the relative-motion joint LL. Further grooves 26 in the surface portion 32 can also be provided, and a lubricant in the grooves 23 and 26 can ease sliding in the joint LL.

The base of the neck is formed with a radially throughgoing hole or radially open recess 22 allowing the metal part 11, 12, 18 of the endoprosthesis 10 to be gripped and withdrawn for replacement and also serving for retaining a tab of the sheath 17. The sheath 17 can be left in the bone 14 as a permanent implant. To this end the outer surface of the sheath 17, as seen in FIG. 5, can be formed with ridges or bumps 28 and grooves 29 so that this sheath 17 can in effect become part of the bone 14.

The arrangement of FIG. 4 is substantially identical to that of FIG. 2, except that two cylindrical portions 20a and 20b separated by a frustoconical region 21 form the distal portion of the stem 18a of the sheath 17a. The sheath has complementarily cylindrical surface portions 32a and 32b in which the portions 20a and 20b can slide along the respective axis $A_D$, and is formed therebetween with an enlargement 24 to prevent any axial force from being transmitted by the portion 21 to the sheath 17. This enlargement 24, like the grooves 23, can form an annular lubricant-filled chamber. In addition FIG. 4 shows how the synthetic-resin sheath 17 has a proximal extension 34 that surrounds the neck 12.

FIG. 6 shows a system wherein a ceramic ball head 11a is fitted on a stub 35 at the outer end of the neck. This arrangement is intended for situations where replacement of the ball is likely to be necessary.

FIGS. 7 and 12 show an arrangement substantially identical to that of FIG. 2, but wherein the stem 18 is of flattened section, having an outer surface 20c of lozenge section, and is fitted in a sheath 17c of corresponding section. It is also possible to have a triangular-section stem 18h and sheath 17h as shown in FIG. 12A, or a cylindrical stem 18i and sheath 17i as shown in FIG. 12B. FIG. 12C has a cylindrical sheath 17j and relatively telescoping and tubular stem parts 18j' and 18j'', the latter of which is fixed in the sheath 17j.

In addition as shown in FIGS. 8 and 13 a teflon or TFE layer 27 can be provided on the outside of the stem 18d or on the inside of the sheath 17d to facilitate axial sliding.

The groove 23 is extended down fairly far in the arrangement of FIG. 9 where a complementary sheath 17e and stem 18e only engage each other in sliding contact over a very short region. The system of FIG. 10 has a sheath 17f provided with a slid insert for the surface 20f of the stem 17f, and in FIG. 11 this insert 25 in fact completely replaces the inner region of the sheath for a surface 20g of a stem 18g.

I claim:

1. A hip endoprosthesis for mounting in a distally tapering recess that opens at the proximal end of a femur, the prosthesis comprising:
    a nonmetallic sheath imbedded in the recess so as to be generally integral with the femur and having an inner surface with a distally tapering proximal portion, a uniform-section distal portion, and an intermediate portion between the proximal and distal portions and generally of greater cross section than the distal portion;

a ball shaped to fit into an acetabulum;

a neck extending distally from this ball and out of engagement with the sheath and femur;

a stem unitarily formed of metal with the neck and ball and engaged in the sheath, the stem having an outer surface with a tapered proximal surface portion complementary to and tightly fitted in the proximal portion of the sheath surface and a uniform-section distal portion in the distal surface portion of the sheath surface, the stem substantially only engaging the sheath at its tapered proximal surface portion and its uniform-section distal portion, the intermedicate portion being spaced from and forming an annular compartment with the stem between the proximal and distal portions; and means between the distal portions of the inner and outer surfaces for relative sliding of the stem and the sheath at the distal portions, whereby relative motion of the proximal surface portions is impossible but relative sliding motion of the distal surface portions is possible.

2. The hip endoprosthesis defined in claim 1 wherein the proximal surface portions are generally frustoconical and the distal surface portions are substantially cylindrical.

3. The hip endoprosthesis defined in claim 1 wherein the sheath is formed with a radially inwardly opening groove forming the compartment.

4. The hip endoprosthesis defined in claim 1 wherein the sheath is provided with a lining sleeve forming the distal sheath surface portion.

5. The hip endoprosthesis defined in claim 1 wherein the distal sheath surface portion is formed with radially inwardly opening grooves.

6. The hip endoprosthesis defined in claim 5 further comprising a lubricant in the grooves.

7. The hip endoprosthesis defined in claim 1 wherein at least one of the distal surface portions has a surface coating with a very low coefficient of friction.

8. The hip endoprosthesis defined in claim 1 wherein the stem distal surface portion is generally cylindrical and stepped, having an inner large-diameter region and an outer smaller-diameter region.

9. The hip endoprosthesis defined in claim 1 wherein the stem is releasably snap-fitted into the sheath.

10. The hip endoprosthesis defined in claim 1 wherein the ball, neck, and proximal surface portions are centered on a proximal axis and the distal surface portions are centered on a distal axis intersecting the proximal axis and defining an obtuse angle therewith.

11. A hip endoprosthesis for mounting in a distally tapering recess that opens at the proximal end of a femur, the prosthesis comprising a nonmetallic sheath imbedded in the recess so as to be generally integral with the femur and having an inner surface with a distally tapering proximal portion, a uniform-section distal portion, and a radially inwardly grooved intermediate portion between the proximal and distal portions and generally of greater cross section than the distal portion;

a ball shaped to fit into an acetabulum;

a neck extending distally from this ball and out of engagement with the sheath and femur;

a stem unitarily formed of metal with the neck and ball and engaged in the sheath, the stem having an outer surface with a tapered proximal surface portion complementary to and tightly fitted in the proximal portion of the sheath surface and a uniform-section distal portion in the distal surface portion of the sheath surface, the stem substantially only engaging the sheath at its tapered proximal surface portion and its uniform-section distal portion, the intermediate portion being spaced from and forming an annular compartment with the stem between the proximal and distal portions; and means between the distal portions of the inner and outer surfaces for relative sliding of the stem and the sheath at the distal portions, whereby relative motion of the proximal surface portions is impossible but relative sliding motion of the distal surface portions is possible.

12. A hip endoprosthesis for mounting in a distally tapering recess that opens at the proximal end of a femur, the prosthesis comprising:

a nometallic sheath imbedded in the recess so as to be generally integral with the femur and having an inner surface with a distally tapering proximal portion, a uniform-section distal portion, and an intermediate portion between the proximal and distal portions and generally of greater cross section than the distal portion;

a ball shaped to fit into an acetabulum;

a neck extending distally from this ball and out of engagement with the sheath and femur;

a stem unitarily formed of metal with the neck and ball and engaged in the sheath, the stem having an outer surface with a tapered proximal surface portion complementary to and tightly fitted in the proximal portion of the sheath surface and a uniform-section distal portion in the distal surface portion of the sheath surface, the stem distal surface portion being generally cylindrical and stepped so as to have an inner large-diameter region and an outer smaller-diameter region, the stem substantially only engaging the sheath at its tapered proximal surface portion and its uniform-section distal portion, the intermediate portion being spaced from and forming an annular compartment with the stem between the proximal and distal portions; and means between the distal portions of the inner and outer surfaces for relative sliding of the stem and the sheath at the distal portions, whereby relative motion of the proximal surface portions is impossible but relative sliding motion of the distal surface portions is possible.

* * * * *